(12) United States Patent
Thassu

(10) Patent No.: US 6,663,892 B1
(45) Date of Patent: Dec. 16, 2003

(54) MULTIPLE PORTION TABLET

(75) Inventor: Deepak K. Thassu, West Henrietta, NY (US)

(73) Assignee: L. Perrigo Company, Allegan, MI (US)

( * ) Notice: Subject to any disclaimer, the term of this patent is extended or adjusted under 35 U.S.C. 154(b) by 0 days.

(21) Appl. No.: 10/223,127

(22) Filed: Aug. 19, 2002

(51) Int. Cl.[7] .................................................. A61K 9/24
(52) U.S. Cl. .................. 424/472; 424/464; 424/682; 424/686; 424/687; 424/688; 424/689; 424/690; 424/692; 424/715; 424/716; 424/717; 514/400
(58) Field of Search ................................. 424/400, 464, 424/472, 682, 686–690, 692, 715–717; 514/400

(56) References Cited

U.S. PATENT DOCUMENTS

| | | |
|---|---|---|
| 701,438 A | 6/1902 | Whyte |
| 2,888,382 A | 5/1959 | Pleyte et al. ................. 167/82 |
| 3,048,526 A | 8/1962 | Boswell ........................ 167/82 |
| 3,125,491 A | 3/1964 | Elowe et al. ................. 167/82 |
| 3,358,687 A | 12/1967 | Miley et al. ................. 128/271 |
| 3,962,107 A | 6/1976 | Levin et al. ................. 252/100 |
| 4,664,915 A | 5/1987 | Simonian .................... 424/128 |
| 4,849,218 A | 7/1989 | Hess et al. .................. 424/94.1 |
| 4,869,908 A | 9/1989 | Kirschner et al. ........... 424/468 |
| 5,085,865 A | 2/1992 | Nayak ......................... 424/422 |
| 5,190,760 A | 3/1993 | Baker ........................... 424/438 |
| 5,229,137 A | 7/1993 | Wolfe .......................... 424/687 |
| 5,571,519 A | 11/1996 | Synodis et al. ............. 424/405 |
| 5,629,026 A | 5/1997 | Davis ........................... 424/686 |
| 5,656,652 A | 8/1997 | Davis ........................... 514/400 |
| 5,681,582 A | 10/1997 | Gilis et al. .................... 424/468 |
| 5,736,158 A | 4/1998 | Quast ........................... 424/464 |
| 5,817,340 A * | 10/1998 | Roche et al. ................. 424/470 |
| 6,039,974 A | 3/2000 | MacLaren et al. .......... 424/472 |
| 6,086,919 A | 7/2000 | Bauer et al. ................. 424/489 |
| 6,183,776 B1 * | 2/2001 | Depui et al. ................. 424/468 |
| 6,254,886 B1 | 7/2001 | Fusca et al. ................. 424/464 |
| 6,319,519 B2 | 11/2001 | Woolfe et al. ............... 424/472 |

* cited by examiner

Primary Examiner—Thurman K. Page
Assistant Examiner—Konata M. George
(74) Attorney, Agent, or Firm—Price, Heneveld, Cooper, DeWitt & Litton

(57) ABSTRACT

A solid orally administrable pharmaceutical dosage form for the treatment of gastric disorders includes a first portion containing a therapeutically effective amount of a histamine $H_2$-receptor antagonist, and a second portion immediately adjacent the first portion without an intervening barrier disposed between the first portion and the second portion, the second portion containing a therapeutically effective amount of an antacid. Physical separation of the active ingredients into two different portions without a separating barrier has been found sufficient to prevent degradation of the histamine $H_2$-receptor antagonist due to contact with the antacid. The invention therefore provides stabilization of a histamine $H_2$-receptor antagonist-antacid combination tablet which is comparable to known multiple portion tablets, but without an intervening barrier between the antacid portion and the histamine $H_2$-receptor antagonist portion. Therefore, the benefits of the prior art are achieved at a reduced cost by eliminating a barrier and manufacturing steps associated with the provision of a barrier, as is conventional.

20 Claims, 1 Drawing Sheet

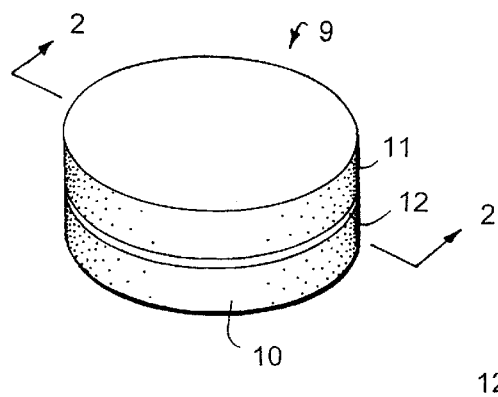
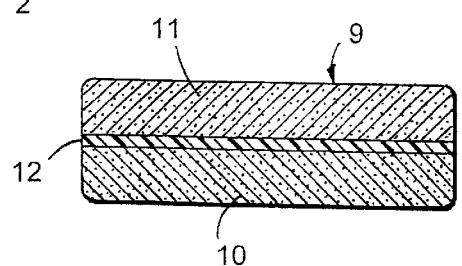
FIG. 1
PRIOR ART
FIG. 2
PRIOR ART
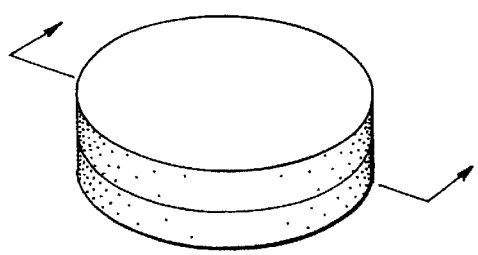
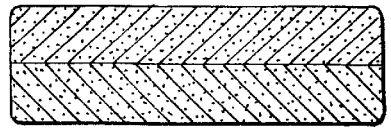
FIG. 3
FIG. 4

MULTIPLE PORTION TABLET

FIELD OF THE INVENTION

This invention relates to pharmaceutical dosage forms for the treatment of gastric disorders, and more particularly to multiple layer or multiple portion solid oral dosage forms comprising a histamine $H_2$-receptor antagonist and an antacid.

BACKGROUND OF THE INVENTION

Gastrointestinal disorders such as acid indigestion, heartburn and gastritis are commonly treated with a histamine $H_2$-receptor antagonist such as cimetidine, ranitidine, nizetidine and famotidine. Histamine $H_2$-receptor antagonists reduce acid secretion by acting directly on the acid-secreting parietal cells located within the gastric gland of the stomach wall.

Antacids such as sodium bicarbonate, calcium carbonate, aluminum hydroxide and magnesium hydroxide are also commonly employed in the treatment of a large variety of nonspecific gastrointestinal symptoms. Antacids react with hydrochloric acid to form salt and water, thereby neutralizing gastric acid and raising gastric pH.

It has also been known to combine a histamine $H_2$-receptor antagonist and an antacid in a single solid dosage form in order to provide immediate relief of pain and discomfort by neutralization of gastric acid with the antacid and independent inhibition of acid secretion with the histamine $H_2$-receptor antagonist. However, it is well known that when histamine $H_2$-receptor antagonists are co-administered with antacids, a substantial reduction in plasma bioavailability of the histamine $H_2$-receptor antagonist is frequently observed. Accordingly, combinations of a histamine $H_2$-receptor and an antacid have been contraindicated.

U.S. Pat. Nos. 5,629,026 and 5,656,652 state that absorption of the histamine $H_2$-receptor antagonist of a solid dosage form containing a histamine $H_2$-receptor antagonist and an antacid may be enhanced by optimally buffering the composition to confer a pH substantially equal to that of the pKa of the histamine $H_2$-receptor antagonist. These patents disclose tablet formulations prepared by blending antacid granules and a histamine $H_2$-receptor antagonist, along with conventional tableting aids, fillers and palatability aids, and tableting on a conventional machine. These patents do not suggest any interaction between the antacid and the histamine $H_2$-receptor antagonist, and do not suggest any need for separating the antacid from the histamine $H_2$-receptor antagonist.

It has been determined that unless special precautions are taken, the histamine $H_2$-receptor antagonist will degrade in the presence of an antacid. U.S. Pat. No. 5,817,340 discloses that degradation of the histamine $H_2$-receptor antagonist can be prevented by interposing a film-forming polymer barrier between the histamine $H_2$-receptor antagonist and the antacid to prevent the therapeutic ingredients from contacting each other. A first of the disclosed embodiments is a tri-layer tablet which includes a first layer containing an antacid, a second layer containing a histamine $H_2$-receptor antagonist, and a barrier layer interposed between the first and second layers. The barrier layer is a film or diaphragm or membrane composed of plastic material which prevents migration of the antacid from the first layer to the second layer, and prevents migration of the histamine $H_2$-receptor antagonist from the second layer to the first layer. An alternative embodiment comprises a core containing a first active ingredient (e.g., the antacid), a polymer barrier coated over the core, and a shell formed over the polymer coated core and containing a second active ingredient (e.g., the histamine $H_2$-receptor antagonist). In another embodiment, granules comprising one of the active ingredients (e.g., the histamine $H_2$-receptor antagonist) are coated with a polymer barrier, and the coated granules are then mixed with the second active ingredient (e.g., the antacid), and pressed into tablets.

Thus, the known orally administrable solid dosage forms containing both an antacid and a histamine $H_2$-receptor antagonist are either prepared without any regard for degradation of the histamine $H_2$-receptor antagonist due to contact with the antacid, or are prepared with a barrier layer between a first portion containing the antacid, and a second portion containing the histamine $H_2$-receptor antagonist.

SUMMARY OF THE INVENTION

This invention is directed to a solid orally administrable pharmaceutical dosage form comprising a first portion including a therapeutically effective amount of a histamine receptor antagonist, and a second portion immediately adjacent the first portion without an intervening barrier layer, the second portion including a therapeutically effective amount of an antacid. More specifically, it has been discovered that the histamine $H_2$-receptor antagonist can be stabilized and protected from degradation induced by contact with the antacid by physically separating the actives into different portions without a discrete barrier layer interposed between the portions.

These and other features, advantages and objects of the present invention will be further understood and appreciated by those skilled in the art by reference to the following specification, claims and appended drawings.

BRIEF DESCRIPTION OF THE DRAWINGS

FIG. 1 is a perspective view of a tri-layer tablet in accordance with the prior art, which includes two active ingredient layers separated by an intervening polymer barrier layer.

FIG. 2 is a cross-sectional view of the prior art tablet shown in FIG. 1, as viewed along lines 2—2 of FIG. 1.

FIG. 3 is a perspective view of a histamine $H_2$-receptor antagonist-antacid bi-layer tablet in accordance with the invention.

FIG. 4 is a cross-sectional view of the bi-layer tablet, as viewed along lines 4—4 of FIG. 3.

DESCRIPTION OF THE PRIOR ART

Shown in FIG. 1 is a tri-layer tablet in accordance with the prior art. The tablet 9 comprises a first portion or layer 10 containing at least one antacid and a second portion or layer 11 containing a guanidinothiazole compound with each of the first and second layers 10, and 11 being separate and discrete from the other layer. Sandwiched between layers 10 and 11 is a barrier 12 which may be a film or diaphragm or membrane composed of plastic material. Alternatively, barrier 12 could also be formed of a compressed pharmaceutically acceptable excipient inert to both the antacid(s) and the guanidinothiazole compound. The pharmaceutical excipient could be formed by compressing the excipient as a middle layer in a multiple layered tablet. Barrier 12 maintains the antacid in first layer 10 out of contact with the guanidinothiazole compound for the treatment of gastric disorders in second layer 11 and prevents migration of the antacid from layer 10 to layer 11 as well as preventing migration of the guanidinothiazole compounds for the treatment of gastric disorders from layer 11 to layer 10.

DESCRIPTION OF THE PREFERRED EMBODIMENTS

Referring to FIGS. 3 and 4, there is shown a tablet 20 according to one of the embodiments of this invention. Tablet 20 includes a first layer or portion 21 containing a histamine $H_2$-receptor antagonist, and a second layer or portion 22 containing at least one antacid. Layers 21 and 22 are substantially homogenous, i.e., the active ingredient in each of the layers 21 and 22 is substantially uniformly distributed throughout the respective layers. Layers 21 and 22 are formed directly adjacent each other, without any intervening barrier layer. It has been discovered that physical separation of the active ingredients into two different portions (e.g., layers) without a separating barrier is sufficient to prevent degradation of the histamine $H_2$-receptor antagonist due to contact with the antacid. Accordingly, the tablets of this invention achieve stabilization of the histamine $H_2$-receptor antagonist which is comparable to that of known multiple portion tablets, but without an intervening barrier between the antacid portion and the histamine $H_2$-receptor antagonist portion. Thus, the benefits of the prior art are achieved with the invention, at a reduced cost, due to the absence of a barrier and manufacturing steps associated with the provision of a barrier.

Suitable histamine $H_2$-receptor antagonists for use in this invention include various guanidinothiazole compounds represented by the formula:

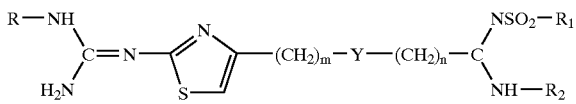

wherein R represents a hydrogen atom or a lower alkyl group; $R_1$ represents an amino group, a mono- or di-lower alkyl amino group, an aryl amino group or an aralkyl amino group; $R_2$ represents a hydrogen atom, a lower alkyl group, a lower alkenyl group or a lower alkynyl group; Y represents a sulfur atom or a methylene group; m and n each represent an integer of 1–3. The term "lower" as used above refers to a straight or branched carbon chain having 1–5 carbon atoms.

Specific examples of histamine $H_2$-receptor antagonists for use in this invention include cimetidine, ranitidine, and famotidine.

The amount of histamine $H_2$-receptor antagonist suitable for treatment of gastric disorder in combination with an antacid(s) should be sufficient to provide a therapeutic dosage to a patient to inhibit the secretion of gastric acid in the treatment of gastric ulcers and duodenal ulcers. The effective amount of histamine $H_2$-receptor antagonist in a combination dosage with effective amounts of an antacid vary from patient to patient depending on the condition of the patient and the particular antacid selected. However, suitable amounts will generally vary from about 20 mg to about 800 mg per day (which may be conveniently administered in one to four doses). The preferred dosage ranges for famotidine in combination with an antacid is from about 5 mg to about 20 mg of famotidine per dose and preferably 10 mg of famotidine per dose. The preferred daily dosage of famotidine is about 20 mg for a 70 kg adult. A preferred adult dose of famotidine and antacid given for a treatment of gastrointestinal distress is 10 mg of famotidine with a sufficient amount of at least one antacid to provide in the range of from about 5 to about 10 ANC. (ANC is determined accordingly to the Federal Register 39-19862, Jun. 4, 1974). A preferred weight ratio of famotidine to an antacid is in the range of from about 1 to 75 to about 1 to 10.

A suitable dose of cimetidine is between 1 mg and 25 mg, preferably between 1 mg and 10 mg. A suitable dose of ranitidine is between 1 mg and 25 mg, preferably between 1 mg and 10 mg, and more preferably between 1 mg and 5 mg.

The antacid used in this invention can be administered in a dosage range of from about 5 ANC to about 160 ANC per dosage unit, preferably from 5 ANC to 20 ANC, wherein the daily dosage does not exceed 160 ANC. The dosage ranges may vary for age and weight of a patient as well as the severity of symptoms.

Suitable antacids for the practice of this invention may be selected from the group consisting of antacids acceptable to the Food and Drug Administration, including, but not limited to, aluminum carbonate, aluminum hydroxide (or as aluminum hydroxide-hexitol stabilized polymer, aluminum hydroxide-magnesium hydroxide co-dried gel, aluminum hydroxide-magnesium trisilicate co-dried gel, aluminum hydroxide-sucrose powder hydrated), aluminum phosphate, aluminum hydroxy carbonate, dihydroxy aluminum sodium carbonate, aluminum magnesium glycinate, dihydroxy aluminum aminoacetate, dihydroxy aluminum aminoacetic acid, bismuth aluminate, bismuth carbonate, bismuth subcarbonate, bismuth subgallate, bismuth subnitrate, calcium carbonate, calcium phosphate, hydrated magnesium aluminate, activated sulfate, magnesium aluminate, magnesium aluminosilicates, magnesium carbonate, magnesium glycinate, magnesium hydroxide, magnesium oxide, magnesium trisilicate, sodium bicarbonate and combinations of two or more of these antacids.

Preferred antacids include antacids selected from the group consisting of aluminum hydroxide, magnesium carbonate, calcium carbonate, magnesium hydroxide and mixtures of two or more of these antacids. Preferred mixtures include mixtures of aluminum hydroxide and calcium carbonate, and mixtures of calcium carbonate and magnesium hydroxide, wherein the antacids are present in an amount sufficient to provide at least 5 ANC and preferably from 5 to 20 ANC.

A therapeutically effective amount of an antacid is an amount which is effective to substantially neutralize gastric acid, i.e., an amount sufficient to reduce gastric pH and reduce pain and discomfort associated with epithetic heartburn, gastritis, and the like. Typical dosages include an amount of antacid having an acid-neutralizing capacity equal to commercially available antacid products. A suitable dose range for magnesium hydroxide is from about 150 mg to 3000 mg, and more typically from about 300 mg to 600 mg. A suitable dose range for aluminum hydroxide is from about 180 mg to 3600 mg, and more typically from about 360 to 720 mg. A suitable dose range for sodium bicarbonate is from about 400 mg to 8000 mg, and more typically from about 800 mg to about 1600 mg.

Various excipients and/or adjuvants may be included as needed or desired. Excipients suitable for use in the dosage forms of this invention include fillers, binders, sweeteners, artificial sweeteners, lubricants, glydants, disintegrants, colors, adsorbents, acidifying agents and flavoring agents. The choice of excipient will depend on the solid oral dosage form desired and whether the dosage is to be chewable or be swallowed whole. Examples of sweeteners include mannitol, dextrose, fructose, sorbitol, sucrose and lactose.

Examples of binders which may be employed include microcrystalline cellulose, alginic acid, acacia acid, carboxymethyl cellulose and hydroxypropyl cellulose. Artificial sweeteners which may be employed include aspartame, sucralose and saccharin. Examples of lubricants which may be employed include magnesium stearate, talc, stearic acid, calcium stearate, zinc stearate, stearic acid, hydrogenated vegetable oil, leucine, glycerides, and sodium stearyl fumarate. Examples of suitable acidifying agents which may be employed include citric acid and malic acid. Examples of fillers which may be employed in this invention include dibasic calcium phosphate dihydrate and monobasic calcium phosphate monohydrate.

Suitable methods for manufacturing the tablets in accordance with this invention are well known in the art.

The tablets shown in FIGS. 3 and 4 may be prepared by blending a first active ingredient (either the antacid or the histamine $H_2$-receptor antagonist) with suitable excipients and/or adjuvants to form a first mixture, compressing the first mixture in a bi-layer tableting press to form a first layer, preparing a second mixture comprising the other active ingredient (either the antacid or the histamine $H_2$-receptor antagonist) and any desired or necessary excipients and/or adjuvants, and compressing the second mixture directly on the first layer to form a second layer without any intervening barrier layer between the first and second layer.

In addition to the bi-layer tablet shown in FIGS. 3 and 4, tri-layer and other multiple layer tablets are encompassed within the principals of this invention provided that at least one of the layers contains a histamine $H_2$-receptor antagonist and a directly adjacent layer contains an antacid, without any intervening barrier layer between the antacid-containing layer and the histamine $H_2$-receptor antagonist-containing layer. For example, a tri-layer tablet may be provided which includes a first layer containing a histamine $H_2$-receptor antagonist such as famotidine, a second layer containing a first antacid such as magnesium hydroxide, and a third layer containing a second antacid such as calcium carbonate. The layers may be arranged and prepared in any order.

Although multiple layered tablets are preferred because they are generally easier to manufacture and generally provide lower interfacial areas between the portions, core-shell type tablet configurations and other geometrical arrangements may be employed without departing from the principals of this invention.

The above description is considered that of the preferred embodiments only. Modifications of the invention will occur to those skilled in the art and to those who make or use the invention. Therefore, it is understood that the embodiments shown in the drawings and described above are merely for illustrative purposes and not intended to limit the scope of the invention, which is defined by the following claims as interpreted according to the principles of patent law, including the doctrine of equivalents.

The invention claimed is:

1. A solid orally administrable pharmaceutical dosage form comprising:
   a first portion containing a therapeutically effective amount of a histamine $H_2$-receptor antagonist; and
   a second portion immediately adjacent the first portion without an intervening barrier disposed between the first portion and the second portion, the second portion containing a therapeutically effective amount of an antacid.

2. The dosage form of claim 1, wherein the histamine $H_2$-receptor antagonist is selected from compounds represented by the formula:

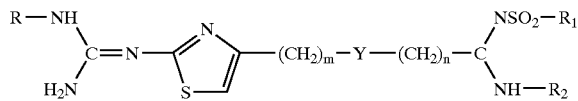

wherein R represents a hydrogen atom or a lower alkyl group; $R_1$ represents an amino group, a mono- or di-lower alkyl amino group, an aryl amino group or an aralkyl amino group; $R_2$ represents a hydrogen atom, a lower alkyl group, a lower alkenyl group or a lower alkynyl group; Y represents a sulfur atom or a methylene group; m and n each represent an integer of 1–3.

3. The dosage form of claim 1, wherein the histamine $H_2$-receptor antagonist is selected from cimetidine, ranitidine and famotidine.

4. The dosage form of claim 1, wherein the antacid is selected from aluminum carbonate, aluminum hydroxide, aluminum phosphate, aluminum hydroxy carbonate, dihydroxy aluminum sodium carbonate, aluminum magnesium glycinate, dihydroxy aluminum aminoacetate, dihydroxy aluminum aminoacetic acid, bismuth aluminate, bismuth carbonate, bismuth subcarbonate, bismuth subgallate, bismuth subnitrate, calcium carbonate, calcium phosphate, hydrated magnesium aluminate, activated sulfate, magnesium aluminate, magnesium aluminosilicates, magnesium carbonate, magnesium glycinate, magnesium hydroxide, magnesium oxide, magnesium trisilicate, sodium bicarbonate and combinations of two or more of these antacids.

5. A solid orally administrable pharmaceutical dosage form comprising:
   a first layer containing a therapeutically effective amount of a histamine $H_2$-receptor antagonist; and
   a second layer immediately adjacent the first layer without an intervening barrier layer disposed between the first layer and the second layer, the second layer containing a therapeutically effective amount of an antacid.

6. The dosage form of claim 5, wherein the histamine $H_2$-receptor antagonist is selected from compounds represented by the formula:

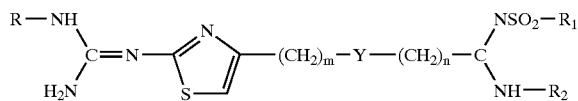

wherein R represents a hydrogen atom or a lower alkyl group; $R_1$ represents an amino group, a mono- or di-lower alkyl amino group, an aryl amino group or an aralkyl amino group; $R_2$ represents a hydrogen atom, a lower alkyl group, a lower alkenyl group or a lower alkynyl group; Y represents a sulfur atom or a methylene group; m and n each represent an integer of 1–3.

7. The dosage form of claim 5, wherein the histamine $H_2$-receptor antagonist is selected from cimetidine, ranitidine and famotidine.

8. The dosage form of claim 5, wherein the antacid is selected from aluminum carbonate, aluminum hydroxide, aluminum phosphate, aluminum hydroxy carbonate, dihydroxy aluminum sodium carbonate, aluminum magnesium glycinate, dihydroxy aluminum aminoacetate, dihydroxy aluminum aminoacetic acid, bismuth aluminate, bismuth carbonate, bismuth subcarbonate, bismuth subgallate, bismuth subnitrate, calcium carbonate, calcium phosphate, hydrated magnesium aluminate, activated sulfate, magnesium aluminate, magnesium aluminosilicates, magnesium carbonate, magnesium glycinate, magnesium hydroxide, magnesium oxide, magnesium trisilicate, sodium bicarbonate and combinations of two or more of these antacids.

9. The dosage form of claim 5, wherein the antacid in the second layer is selected from magnesium hydroxide, calcium carbonate, and a combination of both magnesium hydroxide and calcium carbonate.

10. The dosage form of claim 5, wherein the antacid in the second layer is selected from magnesium hydroxide, calcium carbonate, and a combination of both magnesium hydroxide and calcium carbonate, and wherein the histamine $H_2$-receptor antagonist is famotidine.

11. The dosage form of claim 5, further comprising a third layer containing a second antacid.

12. The dosage form of claim 11, wherein the histamine $H_2$-receptor antagonist is famotidine, the antacid in the second layer is one of magnesium hydroxide and calcium carbonate, and the antacid in the third layer is the other of magnesium hydroxide and calcium carbonate.

13. A process of preparing a multiple layer tablet containing a histamine $H_2$-receptor antagonist and an antacid, comprising:

blending a first active ingredient selected from the antacid and the histamine $H_2$-receptor antagonist with suitable excipients and/or adjuvants to form a first mixture;

compressing the first mixture to form a first layer of the tablet;

blending the other of the antacid and histamine $H_2$-receptor antagonist with excipients and/or adjuvants to form a second mixture; and compressing the second mixture directly on the first layer to form a second layer without any intervening barrier layer between the first layer and second layer.

14. The process of claim 13, wherein the histamine $H_2$-receptor antagonist is selected from compounds represented by the formula:

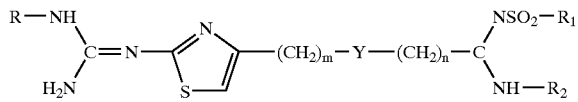

wherein R represents a hydrogen atom or a lower alkyl group; $R_1$ represents an amino group, a mono- or di-lower alkyl amino group, an aryl amino group or an aralkyl amino group; $R_2$ represents a hydrogen atom, a lower alkyl group, a lower alkenyl group or a lower alkynyl group; Y represents a sulfur atom or a methylene group; m and n each represent an integer of 1–3.

15. The process of claim 13, wherein the histamine $H_2$-receptor antagonist is selected from cimetidine, ranitidine and famotidine.

16. The process of claim 13, wherein the antacid is selected from aluminum carbonate, aluminum hydroxide, aluminum phosphate, aluminum hydroxy carbonate, dihydroxy aluminum sodium carbonate, aluminum magnesium glycinate, dihydroxy aluminum aminoacetate, dihydroxy aluminum aminoacetic acid, bismuth aluminate, bismuth carbonate, bismuth subcarbonate, bismuth subgallate, bismuth subnitrate, calcium carbonate, calcium phosphate, hydrated magnesium aluminate, activated sulfate, magnesium aluminate, magnesium aluminosilicates, magnesium carbonate, magnesium glycinate, magnesium hydroxide, magnesium oxide, magnesium trisilicate, sodium bicarbonate and combinations of two or more of these antacids.

17. The process of claim 13, wherein the antacid in the second layer is selected from magnesium hydroxide, calcium carbonate, and a combination of both magnesium hydroxide and calcium carbonate.

18. The process of claim 13, wherein the antacid in the second layer is selected from magnesium hydroxide, calcium carbonate, and a combination of both magnesium hydroxide and calcium carbonate, and wherein the histamine $H_2$-receptor antagonist is famotidine.

19. The process of claim 13, further comprising a third layer containing a second antacid.

20. The process of claim 19, wherein the histamine $H_2$-receptor antagonist is famotidine, the antacid in the second layer is one of magnesium hydroxide and calcium carbonate, and the antacid in the third layer is the other of magnesium hydroxide and calcium carbonate.

* * * * *

UNITED STATES PATENT AND TRADEMARK OFFICE
CERTIFICATE OF CORRECTION

PATENT NO.    : 6,663,892 B1
DATED         : December 16, 2003
INVENTOR(S)   : Deepak K. Thassu It is certified that error appears in the above-identified patent and that said Letters Patent is hereby corrected as shown below:

Column 4,
Line 3, "accordingly" should be -- according --.

Column 5,
Lines 29 and 45, "principals" should be -- principles --.

Signed and Sealed this

Twenty-second Day of June, 2004

JON W. DUDAS
*Acting Director of the United States Patent and Trademark Office*